(12) United States Patent
Mendel-Hartvig et al.

(10) Patent No.: US 7,405,084 B1
(45) Date of Patent: Jul. 29, 2008

US007405084B1

(54) ANALYTICAL METHOD USING PARTICLES AND TEST KIT FOR PERFORMING THE METHOD

(75) Inventors: Ib Mendel-Hartvig, Uppsala (SE); Lena Vinterbäck, Uppsala (SE); Ann Jonsson, Uppsala (SE); Jörgen Gustafsson, Uppsala (SE)

(73) Assignee: Phadia AB, Uppsala (SE)

( * ) Notice: Subject to any disclaimer, the term of this patent is extended or adjusted under 35 U.S.C. 154(b) by 1301 days.

(21) Appl. No.: 09/582,808

(22) PCT Filed: Dec. 30, 1998

(86) PCT No.: PCT/SE98/02462

§ 371 (c)(1),
(2), (4) Date: Oct. 16, 2000

(87) PCT Pub. No.: WO99/36780

PCT Pub. Date: Jul. 22, 1999

(30) Foreign Application Priority Data

Dec. 30, 1997 (SE) .................................... 9704935

(51) Int. Cl.
*G01N 33/543* (2006.01)

(52) U.S. Cl. .................... 436/518; 435/7.92; 435/7.94; 435/970

(58) Field of Classification Search .................. 435/6, 435/7.1, 7.92–7.94, 287.2, 287.1, 287.7, 435/970, 975; 436/514, 518, 535, 536; 422/55–58, 422/61
See application file for complete search history.

(56) References Cited

U.S. PATENT DOCUMENTS

| | | | | |
|---|---|---|---|---|
| 3,720,760 A | * | 3/1973 | Bennich et al. | ............. 436/513 |
| 4,415,700 A | * | 11/1983 | Batz et al. | ................... 524/548 |
| 4,446,231 A | * | 5/1984 | Self et al. | .................. 435/7.91 |
| 4,587,102 A | | 5/1986 | Nagatomo et al. | |
| 4,657,739 A | | 4/1987 | Yasuda et al. | |
| 4,740,468 A | | 4/1988 | Weng et al. | |
| 4,879,215 A | | 11/1989 | Weng et al. | |
| 4,916,056 A | | 4/1990 | Brown, III et al. | |
| 4,981,786 A | * | 1/1991 | Dafforn et al. | .................. 435/7 |
| 5,008,080 A | | 4/1991 | Brown, III et al. | |
| 5,120,643 A | | 6/1992 | Ching et al. | |
| 5,149,622 A | | 9/1992 | Brown et al. | |
| 5,160,701 A | | 11/1992 | Brown, III et al. | |
| 5,190,654 A | | 3/1993 | Bauer | |
| 5,714,389 A | * | 2/1998 | Charlton et al. | ............. 436/514 |
| 5,716,778 A | | 2/1998 | Weng et al. | |
| 5,846,703 A | * | 12/1998 | Devlin et al. | ................... 435/5 |
| 5,902,834 A | * | 5/1999 | Porrvik et al. | ................ 521/62 |

FOREIGN PATENT DOCUMENTS

| | | |
|---|---|---|
| EP | 0200381 | 11/1986 |
| EP | 0284232 | 9/1988 |
| EP | 0420053 | 4/1991 |
| EP | 0437287 | 7/1991 |
| EP | 0462376 | 12/1991 |
| EP | 0472476 | 2/1992 |
| WO | WO8808534 | 11/1988 |
| WO | WO9406012 | 3/1994 |
| WO | WO9622532 | 7/1996 |

* cited by examiner

*Primary Examiner*—Long V. Le
*Assistant Examiner*—Gary W Counts
(74) *Attorney, Agent, or Firm*—Porter Wright Morris & Arthur LLP

(57) ABSTRACT

A method for use in a flow matrix, which utilizes biospecific affinity reactions to detect an analyte in the sample, and which comprises allowing the sample comprising the analyte and an analytically detectable reactant (Reactant*) to migrate through flow channels in a flow matrix to a detection zone located in the matrix, in which there is a firmly anchored biospecific affinity reactant (Capturer), and capturing the Reactant* in the detection zone in an amount related to the amount of analyte in the sample. The Reactant* has labeled particles of an analytically detectable group, and the Capturer is anchored to the matrix by immobilized particles which exhibit hydrophilic groups on their surface. A test kit comprises a flow matrix having a detection zone in which there is a firmly anchored biospecific affinity reactant (Capturer), and an analytically detectable reactant (Reactant*). The Reactant* has labeled particles of an analytically detectable group, and the Capturer is anchored to the matrix by immobilized particles which exhibit hydrophilic groups on their surface.

40 Claims, No Drawings

ANALYTICAL METHOD USING PARTICLES AND TEST KIT FOR PERFORMING THE METHOD

TECHNICAL FIELD

The invention relates to determination methods utilizing biospecific affinity reactions in combination with an analytically detectable reactant (Reactant*) to determine an analyte in a sample. The methods involve utilizing matrices surrounding a liquid flow, which transports analyte and reactants to a detection zone (DZ) in/on the matrix. In the detection zone there is a biospecific affinity reactant (Capturer) firmly anchored to the matrix, which allows for a complex (containing Reactant* and the Capturer) to be formed in the detection zone in an amount reflecting the amount of analyte in the sample. the invention also relates to a test kit for performing the method.

By reactants (including the analyte), exhibiting biospecific affinity (bioaffinity reactants) and which therefore may be utilized in the invention, are meant individual members of the reactant pairs: antigen/hapten-antibody; biotin-avidin/streptavidin; two complementary single chains of nucleic acid etc. As antibodies, antigen binding antibody fragments such as Fab, F(ab)$_2$', single chain Fv (scFv) antibodies etc. are considered. Relevant reactants do not have to be naturally occurring but may also be synthetically prepared molecules/binders.

The type of test methodology in question has previously been used primarily for biospecific affinity reactants where at least one part in a utilized reactant pair has exhibited protein structure, in particular in connection with so called immunochemical determination methods.

The biospecific affinity reactions are primarily performed in aqueous media (e.g. water).

Previously Used Technique

It is previously known how to anchor Capturer to the relevant type of matrices. An alternative has been to achieve this via particles, which have been deposited in/on the matrix. The Capturer has in turn been bound to the particles via bonds which are stable under the conditions used to capture a Reactant* in the detection zone. The bond between Capturer and particle has commonly been covalent but also physical and biospecific adsorption may have been utilized. See inter alia Abbott/Syntex U.S. Pat. No. 4,740,468; Abbott EP 472,476; Hybritech EP 437,287 and EP 200,381; Grace & Co. EP 420,053; Fuji Photo Film U.S. Pat. No. 4,657,739; Boehringer Mannheim WO 94/06012. Label groups suitable to utilize for Reactant* in the relevant type of tests are well known, e.g. particles (Pharmacia AB WO 96/22532; Unilever WO 88/08534; Abbott Laboratories U.S. Pat. No. 5,120,643; Becton Dickinson EP 284,232 etc.). The combination of particles as detectable group and as anchoring particles is also known from several of the publications mentioned above. See e.g. Boehringer Mannheim EP 462,376.

Disadvantages of Previous Technique and Aim of the Invention

In connection with previously known determination methods of the type initially mentioned, there has often been a need for improved detection sensitivity. There has also often been desirable with systems which are easier to produce.

The invention aims at improvements concerning these problems.

The Invention

We have now discovered that anchoring of the Capturer via particles, preferably being smaller than the smallest inner dimension of the flow channels in a flow matrix, is working surprisingly well together with Reactant*, in which the analytically indicatable group is particles. Thus the invention is a test methodology according to what initially has been said and is characterized in that:
A) The analytically detectable reactant (Reactant*) as label group has particles, and
B) The Capturer is anchored to the matrix via particles, having such dimensions that they as such could be transported in the flow passing through the matrix.

The particles should, especially when they are smaller than the flow channels in the matrix, on their surface preferably exhibit hydrophilic groups, which do not belong to the biospecific affinity reactant bound to the particles. Preferred hydrophilic groups are uncharged (usually in the form of alcoholic hydroxyl groups).

In principle, the label particles and anchoring particles may be of the same type, only observing that the anchoring particles do not interfere with the detection of Reactant* in the detection zone.

Particles, intended for anchoring of Capturer in DZ, should, as mentioned above, preferably be smaller than the smallest inner dimension of the flow channels. Suitable particle sizes (largest outer dimension/diameters) are in the interval 0.1-1000 µm, preferably 0.1-100 µm. Considerations must be made in every special case regarding the smallest inner dimension of the flow channels in the matrix to be used. The particles used may be polydisperse or monodisperse. Their shape may vary from spherical to totally irregular. Suitable particle materials which can be mentioned are e.g. $SiO_2$ and other polymeric materials such as organic polymers chosen among (a) synthetic polymers, e.g. condensation polymers, addition polymers etc. Among addition polymers can particularly be mentioned those based on monomers chosen among alkylvinyl ether, arylvinyl ether, vinylarene (such as styrene and divinyl benzene), alkylalkene, acrylate, methacrylate, acrylamide, methacrylamide etc., and (b) biopolymers, e.g. polysaccharides (agarose, dextran, starch) optionally being synthetically cross-linked (an example of semi-synthetic polymer) etc.

In this connection so called latex particles have often been used, which often are polymerized styrene or other polymerized alkene/alkadiene. The anchoring particles may be porous or non-porous.

It is often important to choose anchoring particles being intermediate regarding hydrophobic and hydrophilic features. The reason is that the flow matrices in question often exhibit a marked hydrophobicity although they are sufficiently hydrophilic for allowing a flow of aqueous liquid media. A marked hydrophobic particle, e.g. of polystyrene, is thus adsorbed very strongly to nitrocellulose membranes. The same can also be said for other flow matrices with comparable balance between hydrophilic and hydrophobic features. Unfortunately hydrophobic features of the particles promote non-specific adsorption of Reactant* and/or analyte. This decreases the sensitivity of the test methodology. In our systems we therefore chose to hydrophilize hydrophobic particles, e.g. by on their surface introducing hydrophilic groups, such as hydroxy groups. It is particularly convenient to coat hydrophobic particles with polyhydroxy polymers or other hydrophilic polymers, which preferably should be substituted with hydrophobic groups, e.g. hydrocarbyl groups such as phenyl. As specific examples of usable hydrocarbyl substituted hydrophilic polymers, those having polysaccharide structure, e.g. phenyldextran can be mentioned. Presence of the hydrophobic groups on a hydrophilic polymer facilitates the adsorption of the polymer to hydrophobic particles. This decreases in turn the need of stabilising an adsorbed polymer via cross-linking. In industrial engineering this may be of great importance as cross-linking easily leads to particle aggregation, especially for the particles having the small dimensions often used in connection with the present invention. Introduction of hydrophilic groups on the particles means that covalent binding of biospecific affinity reactants to the particles more easily can be achieved. Also hydrophilisation as such decreases the tendency of non-specific adsorption in the detection zone.

Particles intended for Reactant* to be detectable are usually smaller than those utilized for anchoring. Suitable particle diameters are usually chosen in the interval 0.001-5 µm, often preferably colloidal dimensions, so called sol (i.e. spheric and monodisperse with a size in the interval 0.001-1 µm). In principle the same particle material as for the anchoring particles may be used. Well known label particles are metal particles (e.g. gold sol), non-metal particles ($SiO_2$, carbon, latex (polystyrene) and killed erythrocytes and bacteria). For particles of non-colloidal dimensions it is true that they should be non-sedimentary under the conditions which are valid for transport in the matrix. Thus carbon particles (<1 µm), which have been more or less irregular and more or less polydisperse, have been used (Pharmacia AB, WO 96/22532). The particles may be provided with groups facilitating their detection, e.g. by being provided with chromophore, fluorophore, radioactive compound, enzyme etc. In the invention it has been shown to be unexpectedly advantageous with fluorescent particles rather than coloured particles, such as carbon particles.

The demands for balance between hydrophobic and hydrophilic features for label particles are similar to those being true for the anchoring particles.

When the Capturer with its anchoring particles is deposited in the detection zone it is essential that the conditions are chosen so that physical adsorption to the matrix is promoted. Drying is often essential. When the bonds between matrix and anchoring particles once have been formed it is often difficult to break them. However Reactant* shall be applied under conditions promoting the reactant to be maintained in suspension and does not promote physical adsorption of the particles to the matrix. If Reactant* is to be predeposited in the matrix it is essential that it is made in a way which promotes rapid resuspension for transport in the matrix. Compare below under the heading "Application zone for biospecific affinity reactants other than analyte ($A_R Z$)".

In the detection zone, the analyte may bind directly or indirectly to the Capturer. In the last-mentioned case the Capturer is a biospecific affinity reactant which can bind to an additional reactant which in turn binds to the analyte via biospecific affinity. In this case this additional reactant need not be immobilized in the matrix from the beginning, but may be movably (diffusively) pre-deposited in the matrix in an area or zone separated from the detection zone, or it may be added together with or separately from the sample. If this additional reactant is in soluble form, the Capturer is advantageously one member of a specific binding pair, the other member of which is coupled or conjugated to the reactant. Examples of such specific binding pairs are immunological binding pairs, such as antigen-antibody and hapten-antibody, biotin-avidin or -streptavidin, lectin-sugar, nucleic acid duplex.

The particle system according to the invention is particularly advantageous for allergy tests, where the allergen with which the analyte (most often of IgE class) is to react usually is a complex mixture of up to 100 or even more different proteins. By covalent coupling of the proteins to particles and predeposition thereof, a very robustly immobilized allergen is obtained, which allergen in contrast to allergen which is passively adsorbed to a matrix does not leak selectively more of certain components. This in combination with the fact that particle labels give a very good signal results in an extraordinary test system for allergy. The above applies to all tests where complex binders are used, e.g. autoantigens in the determination of autoimmune disease.

A variant with soluble reactant (allergen) which is predeposited or is added together with the sample may also give other advantages in allergy tests, since on the one hand, the incubation time between particle label and allergen/analyte will be considerably longer, and, on the other hand, a soluble allergen is more available for reaction with the analyte than when the allergen is bound to a solid phase.

Matrices

The matrix defines the space in which the reactants are transported. The matrix may be the inner surface of a single flow channel (e.g. a capillary), the inner surface of a porous matrix having a system of flow channels extending through, etc. This type of matrices is called flow matrices below. Flow matrices may exist in the form of monoliths, sheets, columns, membranes, single flow channels having capillary dimensions or aggregated systems of such flow channels etc. They may also exist in the form of particles packed in column casings, compressed fibres etc. The inner surface of the matrices should be hydrophilic, so that aqueous media (usually water) may be absorbed and transported through the matrices. The smallest inner dimension of the flow channels should be sufficiently large for allowing transport through the matrix of the reactants used. The rule of thumb is that suitable matrices are selectable among those having flow channels with the smallest inner dimension in the interval 0.4-1000 µm, preferably 0, 4-100 µm if the matrix has a system of mutually communicating flow channels. Flow channels having the smallest inner dimension in the upper part of the broad interval (up to 1000 µm) are primarily of interest for flow driven by an externally applied pressure/sucking.

Matrices of interest are often built up from a polymer, e.g. nitrocellulose, nylon etc. The material in the matrix as well as the physical and geometrical design of the flow channels may vary along the flow depending on what a certain part of the matrix is to be utilized for (Pharmacia AB WO 96/22532; Medix WO 94/15215).

Along the transport flow in the matrix there may be defined zones for application of sample ($A_S Z$), reactants ($A_R Z$) buffer ($A_B Z$), etc. and zones for detection (DZ) and calibrator (CZ, see below).

Flow matrices, which may be used in the particular type of tests, are described in previous patent publications (Behringwerke U.S. Pat. No. 4,861,711; Unilever WO 88/08534; Abbott U.S. Pat. No. 5,120,643 and U.S. Pat. No. 4,740,468; Becton Dickinson EP 284.232 and U.S. Pat. No. 4,855,240; Pharmacia AB WO 96/22532 etc.).

Transport Flow

The direction of the transport flow is from an application zone towards a detection zone (DZ). Exactly which zones the transport flow will pass is determined by the particular test protocol. A transport flow may start from a point with radial spread and a flow front in the form of a circular periphery or a part thereof. A transport flow may also start from a zone in the form of a hand and may have a straight flow front perpendicular to the direction of flow.

In a less preferred variant the transport flow proceeds from an application zone for sample, which at the same time is a zone for detection. The flow in this variant is spread out from the application/detection zone, preferably radially, and may possibly pass additional downstream detection zones.

The transport flow through the particular types of matrix may be achieved by influence of capillary forces, e.g. by starting off with a substantially dry matrix. As an aid a sucking body may be placed at the end of the flow. Flow, meaning transport mainly only of dissolved components, may be achieved if an electrical field is imposed across the matrix (in the flow direction).

The utilized flow is preferably lateral, i.e. parallel with the upper surface of the matrix. Also other types of flow (in depth in the matrix) may be used.

Relevant Test Protocols

The invention may primarily be applied to non-competitive (non-inhibition) test variants but also to competitive (inhibition) test variants. The complexes being formed in different test protocols are described schematically below. It has been assumed that relevant reactants are monovalent regarding utilized binding sites. The protocols may be run as simultaneous or sequential variants regarding analyte and an added reactant. By simultaneous variants is meant that the analyte (sample) and the reactant in question migrate together at least during some part of the transport and preferably reach the detection zone simultaneously. By sequential variants is meant that the analyte (sample) at least during some part of the transport towards the detection zone migrates before a reactant and preferably reaches the detection zone before the reactant. The test protocols of the invention should always be simultaneous or sequential regarding analyte and Reactant*. "-" relates to firm anchoring from the start. " - - - " relates to binding via biospecific affinity.

A. Sandwich Protocol:

Capturer and Reactant* have biospecific affinity for the analyte. x is the number of moles of Capturer on the matrix. y is the number of moles of analyte (=the number of moles of Reactant*), being bound to the Capturer.

Complex formed in the detection zone:

$$\text{Matrix }(\text{-Capturer})_{x-y}(\text{-Capturer - - - analyte - - - Reactant*})_y.$$

B. Sandwich Protocol:

The Capturer has biospecific affinity for Reactant I, which in turn has biospecific affinity for the analyte. Reactant* has biospecific affinity for the analyte. x is the number of moles of Capturer on the matrix. y is the number of moles of analyte (=the number of moles of Reactant*), being bound to the Capturer via Reactant I. y+z is the number of moles of Reactant I being bound to Capturer.

Complex formed in the detection zone:

$$\text{Matrix }(\text{-Capturer})_{x-z-y}(\text{-Capturer - - - Reactant I})_z(\text{-Capturer - - - Reactant I - - - analyte - - - Reactant*})_y.$$

C. Inhibition Protocol:

The Capturer is an analyte analogue and has binding sites equivalent to binding sites on the analyte. Reactant II has biospecific affinity to the analyte and to Capturer. Reactant* has biospecific affinity to Reactant II. x is the number of moles of Capturer on the matrix. y is the number of moles of Reactant II (=the number of moles of Reactant*), being bound to the matrix via Capturer. Reactant II is part of the complex in an amount related to the amount of analyte in the sample.

Complex formed in the detection zone:

$$\text{Matrix}(\text{-Capturer})_{x-y}(\text{-Capturer - - - Reactant II - - - Reactant*})_y.$$

D. Inhibition Protocol:

The Capturer exhibits biospecific affinity for both analyte and Reactant*. Reactant* is a detectable soluble analyte analogue. x and y are the number of moles of Reactant* and analyte respectively, being bound to the matrix via Capturer. x+y is the number of moles of Capturer on the matrix.

Complex formed in the detection zone:

$$\text{Matrix}(\text{-Capturer - - - Reactant*})_x(\text{-Capturer - - - analyte})_y.$$

Application Zone for Sample ($A_SZ$)

This type of zone is to be found upstream of the detection zones for the intended analyte.

Application Zone for Biospecific Affinity Reactants Other than Analyte ($A_RZ$)

The sequence of the application zones should ensure that the test protocols are simultaneous or sequential regarding analyte and Reactant*. This means that the application zone for reactants ($A_RZ$), inclusive for Reactant* ($A_{R*}Z$), should always be upstream of the detection zone. One or more reactants may be added in the same application zone. If the application zone is common to sample and at least one reactant ($=A_RZ/A_SZ$), e.g. Reactant* ($=A_R*Z/A_SZ$), application may be performed simultaneously, e.g. that a sample and reactant are mixed before being applied in the zone. If desired the mixture may be pre-incubated so that the reactant binds in an intended way to the analyte or other components in the sample before application. One skilled in the art may with knowledge of different protocols easily determine which zones will be needed and in which order they are to be positioned.

Reactants being utilized in the method may be pre-deposited in the respective zone or be added when the determination method is performed. Pre-deposition means that the reactant in question is applied in advance and in such a way that it does not spread in the matrix until flow is initiated.

Pre-deposition of reactants may take place by methods known per se. (See e.g. Behringwerke U.S. Pat. No. 4,861,711; Unilever WO 88/08534; Abbott U.S. Pat. No. 5,120,643; Becton Dickinson EP 284.232). It is important to take into consideration that the reactant in question should be able to dissolve when a liquid reaches a predeposited reactant. To ensure quick dissolution it is common to incorporate relevant reactants in substances being quickly dissolved by contact with the liquid medium used. This type of substances are often hydrophilic having polar and/or charged groups, such as hydroxy, carboxy, amino, sulphonate etc. In particular may be mentioned hydrophilic quickly soluble polymers, e.g. having carbohydrate structure, simple sugars including mono-, di- and oligosaccharides and corresponding sugar alcohols (mannitol, sorbitol etc.). It is common practice to first coat the relevant application zone with a layer of the quickly soluble substance, and then the reactant is applied, optionally followed by an additional layer of quickly soluble substance. An alternative way is to incorporate the reactant in particles of quickly soluble material which then are deposited in the relevant zone of the matrix.

Zones for Buffer ($A_BZ$)

Essential buffer systems may be included in solutions added simultaneously with samples and reactants. In conventional technique addition of buffer takes place in the application zone upstream of the other application zones. This has usually been equal to sample application zone. In the present invention application of buffer may be performed in optional position (see below).

In a co-pending PCT application "Analytical method comprising addition in two or more positions and a device and test kit therefor" (based on SE 9704934-0) we describe an invention which in one variant provides a preferred embodiment of the present invention. The patent application is incorporated herein by reference. The invention in this separate patent application is based upon the discovery that liquid from two subsequent zones (AZ2 and AZ1) in a flow matrix may migrate after each other without being mixed, if liquid is applied to the downstream zone (AZ1) simultaneously or before applying liquid to the upstream zone. This has led to the possibility to achieve zonewise migration of optional reactants, included in the liquids, towards a detection zone. If the application zone for sample ($A_SZ$) is placed downstream of the application zone for Reactant* ($A_{R*}Z$), the test protocol becomes sequential regarding Reactant*. Having an application zone only for liquid (buffer) ($A_BZ$) between ($A_{R*}Z$) and ($A_SZ$) a wash of the detection zone DZ is performed between capture of analyte and capture of Reactant*. Such an intermediate buffer zone ($A_BZ$) may also ensure that a reactant (including analyte), that is applied in a downstream zone, reaches DZ before a reactant, starting from an upstream application zone for liquid. The latter may be important if the matrix as such retards the reactant that has been applied in the downstream zone.

Reactants may be included in the liquid that is applied to a zone. Alternatively, they may be predeposited in the zone where the corresponding liquid is to be applied or in a zone positioned between this and the nearest downstream zone for application of liquid.

This separate invention allows for application of buffer in the present invention to be performed in optional position. According to conventional technique addition of buffer has only been possible in the application zone, upstream of the other application zones.

This embodiment of the invention is particularly interesting for methods being sequential regarding Reactant*.

Analytes

The invention is primarily adapted for determination of biospecific affinity reactants of the types initially mentioned. The analyte may be a cell or a virus or a part thereof. In particular antigen may be mentioned, such as an immunoglobulin or an antibody. For immunoglobulins the determination may relate to a certain Ig and/or a certain Ig subclass. For antibody the determination may relate to a certain specificity, optionally also the Ig class or Ig subclass of the antibody. Relevant Ig classes are IgA, IgD, IgE, IgG and IgM. Relevant Ig subclasses are IgG1, IgG2, IgG3 and IgG4.

In sandwich variants (according to protocols A and B above) the analyte may be an antibody, directed to an allergen/antigen/hapten, and derive from a certain species, a certain Ig class or a certain Ig subclass. In this case Reactant* may be an analytically detectable antibody directed to an epitope being specific for the species, Ig class or Ig subclass with Capturer (protocol A) and Reactant I (protocol B) as the allergen/antigen/hapten. Alternatively the reverse is chosen i.e. Capturer and Reactant I, respectively, is the antibody directed to the analyte. In the case where the analyte is an antigen in general, for protocol A both the Capturer and Reactant* may be antibodies directed to the antigen. For protocol B it is Reactant I and Reactant* that are antibodies directed to the antigen.

Competitive variants are the most interesting for low molecular analytes. Illustrative examples are antigen and hapten. For protocol C the Capturer may be the antigen or the hapten, firmly anchored to the matrix, Reactant II may be an antibody, directed to the antigen, and Reactant* may be an antibody directed to Reactant II. For protocol D the Capturer may be an antibody directed to the analyte and Reactant* may be the analyte labelled with an analytically detectable group.

The method of the invention may be performed as part of diagnosing allergy or autoimmune disease.

It has been particularly interesting for the inventors to measure anti-allergen antibodies of IgE or IgG class, for the latter preferably with emphasis on some of the mentioned subclasses. Measurement of allergen-specific antibodies may be utilized in connection with diagnosing of IgE mediated allergy.

The invention has, as already mentioned above, proved to be particularly suitable in the case where the Capturer consists of a mixture of different components, e.g. allergen, which often consist of mixtures of several different allergenic components and where the analyte is antibodies directed to individual components in the mixture.

Samples

Relevant samples may be of biological origin, e.g. from different body fluids (whole blood, serum, plasma, urine, tear fluid, cerebrospinal fluid etc.), from cell culture media, processing procedures in biotechnology, from food stuff, from the environment (environment analysis samples) etc. The samples may be pre-treated in order to fit e.g. the matrix, the test protocol involved etc.

Calibrators

Determination methods of the type to which the invention relates involves measurement of the detectable signal from the analytically detectable reactant (Reactant*) and the measured signal (sample value) is taken as a measure of the amount of analyte in the sample. To transfer the measurement signal to actual amounts of analyte the signal is usually compared to the corresponding signal (calibrator value) of known standard amounts of analyte (calibrators). In connection with the present invention a new calibrator system has been developed which applied to the present invention constitutes a best embodiment.

This separate invention means that the used calibrator in advance has been anchored to a matrix (matrix calibrator), preferably of the same type as the one utilized for sample run. When measuring the calibrator values matrix calibrator is allowed to bind to Reactant* and then the measurement signal from Reactant* is measured in a way known per se. By utilizing different amounts of matrix calibrator a series of calibrator values may be obtained corresponding to different pre-determined amounts of analyte in sample (standard amounts, dose response curve, calibration curve).

Instead of anchoring the calibrator in advance to the matrix, a reactant capable of binding the calibrator may be anchored and the calibrator is then added in connection with the determination of calibrator value. When a calibrator binder is bound to the matrix, the calibrator may either be movably (diffusively) pre-deposited in the matrix in a zone or area separated from the detection zone, or may be added together with or separately from the sample.

Applied to the present invention our new calibrator system primarily involves that the transport flow passes one or more zones with a calibrator firmly anchored to the matrix in the respective calibrator zone (KZ).

Anchoring of a calibrator or a calibrator binder to the matrix in a calibrator zone may be performed according to the same principles as for anchoring of Reactant I to a detection zone. The calibrator binder is usually one member of a specific binding pair (reactant pair), the other member of the binding pair being coupled or conjugated to the calibrator substance. Examples of such specific binding pairs have been mentioned above in connection with the description of the Capturer.

Calibrator zones should be located downstream of the application zone for liquid, intended for transport of Reactant*. In relation to the detection zone (DZ), the calibrator zone is preferably located upstream.

Our invention relating to calibrators is described in detail in our co-pending PCT application with the title "A method using a new calibrator and a device and test kit including the calibrator" (based on SE 9704933-2). This application is incorporated herein by reference.

A Second Main Aspect of the Invention

This aspect of the invention is a kit exhibiting (a) an analytically detectable biospecific affinity reactant (Reactant*), in which the label group is particles, together with (b) a flow matrix having a detection zone in which a Capturer is firmly anchored via particles which preferably are smaller than the smallest inner dimension of the flow channels. Relevant particles and flow channels are according to what has been mentioned above. The flow matrix may exhibit application zones, pre-deposited reactants etc. according to the above.

The invention is illustrated in the experimental part and defined in the claims.

EXAMPLE 1

Comparison Between Birch Allergen Bound Via Particles or Directly Adsorbed to the Detection Zone The example is based on determination of IgE specific to birch allergen. To show the strength of the invention the response obtained with a number of patient samples is compared in a test variant where 1) the allergen extract has been coupled covalently to polystyrene particles coated with phenyldextran deposited in the detection zone with 2) allergen extract directly deposited and passively bound to a nitrocellulose membrane.

Methods and Materials

Adsorption of phenyldextran to polystyrene particles: Phenyldextran (substitution degree: 1 phenyl group on each fifth monosaccharide unit=20%, Mw dextran 40,000, Pharmacia Biotech AB, Uppsala, Sweden) dissolved in deionized water to various concentrations was adsorbed with stirring to polystyrene particles (0.49 µm, Bangs Laboratories): 1) 4-5 mg/ml, 8-10% particle suspension, RT 0.5 h; 2) 5 mg/ml, 5% particle suspension, RT, 1 h; 3) 20 mg/ml, 2% particle suspension, overnight. The particles were then washed twice in deionized water. The particle suspension was centrifuged between each incubation and wash (12,100 g, 30 minutes, Beckman J2-21).

Extraction of t3 (birch pollen. *Betula verrucosa*): 1 part (weight) of birch pollen (Allergon, Sweden) was extracted with 10 parts (volume) of 0.1 M of phosphate buffer, pH 7.4. The extraction was continued for 2 h on a shaker table (200 pulses/minute) at +4° C. The extract was centrifuged at 4000 rpm for 1.75 h. After filtration the t3-extract was applied to a PD-10 column (Pharmacia Biotech AB, Sweden) and eluted in 0.1 M $NaHCO_3$, pH 8.5. The t3-eluate (designated: t3-extract 1/14) was taken to amino acid analysis for determination of the total level of protein.

Coupling of t3-extract to polystyrene particles (t3-particles): t3-extract was coupled to phenyldextran coated polystyrene particles with CDAP (1-cyano-4-dimethylamino-pyridinium bromide) (Kohn J and Wilchek M, FEBS Letters 154(1) (1983) 209-210).

Polystyrene particles (2128 mg) coated with phenyldextran in 30% (by volume) acetone, 2% particle suspension, were activated with 954 mg CDAP (100 mg/ml in 30% acetone) and 7.63 ml of 0.2 M triethylamine (TEA, Riedel-de Haen, Germany). CDAP was added with stirring and TEA was added dropwise for 90 seconds and stirring for a total of 120 s. The reaction was stopped by addition of 30% acetone (4 fold the volume) and centrifugation at 12,400 g for 35 minutes. The particles were washed once with deionized water.

640 ml of t3-extract 1/14 in 0.1 M $NaHCO_3$, pH 8.5, were added to the activated particles and the coupling reaction was performed for 1 h on a shaker table. The suspension was centrifuged and decanted before the particles were deactivated with 0.05 M aspartic acid and 0.05 M glutamic acid in 0.1 M $NaHCO_3$, pH 8.5. Incubation was effected on a shaker table overnight at +4° C. The particles were washed by centrifugation twice with 50 mM $NaPO_4$, 0.05% $NaN_3$, pH 7.4.

The concentration of particles was determined by a spectrophotometer at 600 nm with uncoated polystyrene particles as a reference. t3-coupled polystyrene particles were taken to amino acid analysis for determination of the total level of protein.

Deposition of t3-extract and t3-particles on membrane (detection zone): To sheets of nitrocellulose with a polyester backing (Whatman, 8 µm, width 5 cm) zones of t3-extract 1/14 were applied with Linear Striper (IVEK Corporation) with a flow of 1 µl/s and 1 µl/cm. The t3-extract 1/14 was deposited undiluted and also diluted 1:1 in 0.1 M $NaHCO_3$, pH 8.5 (t3-extract 1/28). T3-particles were diluted to 4% particle level in 50 mM $NaPO_4$, 6% lactose, 0.05% $NaN_3$, pH 7.4.

Sheets with deposited material were dried for 1 hour at 30° C. The sheets were cut into strips with a width of 0.5 cm (Matrix 1201 Membrane Cutter, Kinematics Automation).

Carbon particle conjugate (Reactant*): Monoclonal anti-human IgE antibody (anti-hIgE) was adsorbed to carbon particles (sp100, <1 µm, Degussa, Germany) according to WO 96/22532. The final suspension diluted in test buffer contained 300 µg/ml carbon particles.

Test methodology: Strips were mounted on a surface inclined about 16° from the bench plane. Sucking membranes (width 3 cm, Whatman, 17 Chr) were placed 0.5 cm into the end of the strip. To obtain a constant pressure metal weights were put on the sucking membranes.

Samples and reagents were pipetted in the order below. Each sample and reagent volume was allowed to migrate into the membrane before the subsequent volume was pipetted.

1) 30 µl of test buffer (0.1 M Tris-HCl, 0.6 M NaCl, 10% sucrose, 3% bovine serum albumin, 0.05% bovine gamma-globulin, pH 7.4)
2) 30 µl serum sample
3) 20 µl of test buffer (the same as in step 1)
4) 20 µl of carbon particle conjugate (anti-hIgE antibody adsorbed to carbon particles, 300 µg/ml, diluted in test buffer)
5) 2×30 µl of test buffer 6) The carbon blackening of the detection zone was measured as absorbance with Ultroscan XL, Enhanced Laser Densiometer (LKB).

RESULTS

Amount of Protein in the Detection Zone

TABLE 1

Deposited amount of t3 in the detection zone

| Deposition solution/ suspension | Amount of protein in reaction zone per 0.5 cm strip (ng) |
|---|---|
| t3-extract 1/14 | 410 |
| t3-extract 1/28 | 205 |
| t3-coupled particles (4%) | 226 |

TABLE 2

Lateral immuno-chromatography with (i) directly adsorbed t3-extract and (ii) t3-coupled particles in the detection zone. Uptake of t3 positive and negative serum samples, determined concerning concentration with Pharmacia CAP system (Pharmacia & Upjohn Diagnostics AB, Sweden).

| Deposition solution/ suspension | 35534 (1.8 KU/L) | 35696 (3.1 KU/L) | 35711 (29.4 KU/L) | 36429 (neg, <0.35 KU/L) |
|---|---|---|---|---|
| t3-extract 1/14 | 5* | 6 | 3 | 0 |
| t3-extract 1/28 | 5 | 0 | 0 | 0 |
| 4% t3-coupled particles | 106 | 64 | 474 | 18 |

*= Absorbance (×1000) in the reaction zone when the label has been bound.

CONCLUSION

The experiments show that the same amount of birch allergen deposited in the form of coupled particles gives significantly higher binding of birch-specific IgE-antibodies as compared to when the allergen is deposited directly on the membrane.

In similar experiments different monodisperse polystyrene particles (Bangs Laboratories) were used as anchoring particles and instead of carbon particles, different diameters of fluorescent polystyrene were used. The diameters of the anchoring particles varied in the different experiments in the interval 0.28-3 µm. The diameters of the label particles varied in the different experiments in the interval 0.1-0.5 µm. The results followed generally the results for carbon particles as presented in detail above.

EXAMPLE 2

Determination of Birch-Specific IgE with Test Variant where Allergens have been Pre-Deposited in the Application Zone Methods and Materials Biotinylation of birch pollen allergen: Extraction of t3 (birch pollen; *Betula verrucosa*) was performed as described previously except that the centrifuged and filtrated solution was applied to a PD-10 column and eluted into deionized water. The t3-eluate was freeze-dried (LSL SECFROID, LYOLAB F, pump: LEYBOLD TRIVAC D8B).

Freeze-dried t3-material was dissolved in 0.15 M $KPO_4$, 0.15 M NaCl, pH 7.8. Determination of content was performed by aminoacid analysis. To the material was added $^{125}$I-labelled t3 and the mixture was applied to a PD-10 column equilibrated with 25 ml of 0.15 M $KPO_4$, 0.15 M NaCl, pH 7.8. Biotinylation of t3-allergen was carried out according to recommended conditions from the supplier (Pierce). To 3 mg of eluted t3-extract (2.0 ml) was then added 0.138 ml of biotin-LC-Sulfo-NHS (3.59 mM, Pierce), and incubation was performed on a shaker for 1 hour at room temperature. The coupling reaction was stopped by the addition of 50 µL of 2 M glycine. The extract was then applied to a gel filtration column PD-10 equilibrated with 50 mM $NaPO_4$, 0.15 M NaCl, pH 7.4. Yields and final protein concentration were determined from the obtained radioactivity.

Coupling of streptavidin to polystyrene particles: Streptavidin (Molecular Probes) was covalently coupled to phenyl-dextran-adsorbed polystyrene particles with CDAP (1-cyano-4-dimethylamino-pyridinium bromide) (Kohn J and Wilchek M, FEBS Letters 154(1) (1983) 209-210).

Desalting and buffer change of streptavidin was performed by gel filtration (PD-10) in $NaHCO_3$, 0.1 M, pH 8.5. 600 mg of phenyldextran-coated polystyrene particles in a 2% solution in 30% (by volume) acetone were activated by 4.5 ml of CDAP (0.44 M) and 3.6 ml of TEA (0.2 M triethylamine, Riedel-deHaën). CDAP was added with stirring for 60 seconds and TEA for 120 seconds. The particles were then washed with 30% (by volume) acetone and centrifuged at 12,100 g (25 minutes, Beckman, J-21, JA-20, 10,000 rpm).

20.6 mg of streptavidin were coupled to 350 mg of activated particles with incubation on a shaker for 1.5 hours at +4° C. The particles were then centrifuged before deactivation was carried out with 0.05 M glutamic acid and 0.05 M aspartic acid in $NaHCO_3$ buffer. Incubation was effected with stirring overnight at +4° C. The coupled particles were then washed twice with 50 mM $NaPO_4$, 0.05% $NaN_3$, pH 7.4.

The particle concentration was determined spectrophotometrically at A 600 nm with untreated particles as reference.

Deposition of streptavidin-coupled particles on nitrocellulose membranes: To sheets of nitrocellulose with a polyester backing (Whatman, 8 µm, 5 cm width) zones of streptavidin-coupled particles diluted to 1% particle content in 10 mM NaPO4, 5% sucrose, 5% dextran 5000, pH 7.4, were applied with a Linear Striper (IVEK Corporation).

The deposition flow was 2.5 µl/cm and the rate 20 mm/sec. The deposits were dried for 1 hour at 30° C., whereupon the sheets were cut to 0.5 cm wide strips (Matrix 1201 Membrane Cutter, Kinematics Automation).

Deposition of biotinylated allergen on filter paper: 10×5 mm filters were cut from filter papers (Whatman 3). 10 µl of biotinylated t3 (77 ng) in 50 mM phosphate buffer, pH 7.4, BSA 6%, were dispensed to the filters, and the filters were dried at 30° C. for 45 minutes.

Coupling of anti-hIgE antibodies to detection particles: Antibodies to hIgE cleaved with pepsin to fab' 2 fragments were coupled to fluorescent polystyrene particles having aldehyde groups on their surface (Molecular Probes C-17177 TransFluoSpheres, aldehyde-sulphate microspheres, 0.1 µm, 633/720, 2% solids). 23 mg of antibody were coupled to 66 mg of particles in 50 mM $NaPO_4$ buffer, pH 6, overnight at room temperature. Then 205 µL of $NaCNBH_4$(5 M) were added to reduce the coupling for 3 hours at room temperature. After centrifugation at 20,800×g (50 minutes in Eppendorf 5417R, 14,000 rpm), deactivation was performed in 0.05 M glutamic acid and 0.05 M aspartic acid in deionized water, pH 6.5, overnight with stirring at room temperature. Centrifugation was then carried out at 20,800×g (50 min). After blocking with 0.2% BSA in 50 mM NaPO$_4$, pH 7.4, with 0.05% NaN$_3$ and incubation overnight at +4° C., centrifugation was performed again at 20,800×g (50 min).

Washing twice with and storage in blocking buffer was then done. The particle concentration was determined in a fluorimeter (Perkin-Elmer LS50B) with a standard curve prepared with the original particle. Coupled protein concentration was determined by having radioactive anti-hIgE present during the coupling.

Test procedure: Strips were mounted to a surface inclined about 16° from the bench plane. Sucking membranes (3.5 cm width, Schleicher & Schuell, GB004) were placed 0.5 cm into the upper end of the strip. To obtain constant pressure, metal weights were placed on the sucking membranes. Samples and reagents were then pipetted successively as described below. Each sample and reagent volume was sucked into the membrane before the following volume was pipetted.

1) Prewash with 30 µl of 50 mM NaPO$_4$, 0.15 M NaCl, pH 7.4.

2) A filter with predeposited biotinylated IgE was placed at the bottom of the strip.

3) 30 µl of serum were pipetted to each filter.

4) 20 µl of test buffer (0.1 NaPO$_4$, 0.15 M NaCl, 10% sucrose, 3% BSA, 0.05% bovine gammaglobulin, 0.05% NaN$_3$, pH 7.4) were added to the filter.

5) The allergen filter was removed.

6) 20 µl of detection conjugate (75 µg/ml) diluted in test buffer.

7) 2×30 µl of test buffer.

8) The fluorescence of the detection zone was measured as a response area (Vmm) with a scanning red laser fluorometer (635 nm).

Selected serum samples included negative, weakly positive and a high positive serum.

RESULTS

| Sample | IgE conc. (KU/L) | Group | Response area (Vmm) |
| --- | --- | --- | --- |
| 35517 | 0.7 | weakly pos. | 0.083 |
| 35713 | 0.8 | weakly pos. | 0.037 |
| 35803 | 0.9 | weakly pos. | 0.361 |
| 35805 | 1.1 | weakly pos. | 0.166 |
| 37692 | neg. | neg. | 0.001 |
| 35592 | neg. | neg. | 0.096 |
| 35593 | neg. | neg. | 0.006 |
| 35599 | neg. | neg. | 0.002 |
| 35716 | 54 | pos. | 2.507 |

The results show that the principle of predeposited allergens (or antigens) in the application zone and a general binder in the reaction zone functions well.

The invention claimed is:

1. A method for detecting an analyte in a sample in a flow matrix by use of biospecific affinity reaction, which method comprises:
    i. allowing an analytically detectable reactant (Reactant*) and a sample comprising the analyte to migrate through flow channels in a flow matrix to a detection zone (DZ) located in the matrix, in which there is a firmly anchored biospecific affinity reactant (Capturer), and
    ii. capturing the Reactant* in the DZ in an amount related to the amount of analyte in the sample,
wherein
    A) the Reactant* has labeled particles as an analytically detectable group, and
    B) the Capturer is anchored to the matrix by immobilized particles which exhibit hydrophilic groups on their surface, wherein the hydrophilic groups are hydroxy, carboxy, amino or sulphonate groups and wherein the particles anchoring the Capturer have a diameter smaller than a smallest inner dimension of the flow channels of the flow matrix and do not interfere with detection of Reactant* in the detection zone.

2. The method according to claim 1, wherein immobilization of a biospecific affinity reactant by covalent binding is to the hydrophilic groups on the Capturer particles.

3. The method according to claim 1, wherein a mixture of biospecific affinity reactants is immobilized to the hydrophilic groups on the Capturer particles.

4. The method according to claim 1, wherein a mixture of biospecific affinity reactants found in allergen extracts is immobilized to the hydrophilic groups on the Capturer particles.

5. The method according to claim 1, wherein a mixture of biospecific affinity reactants found in biological material used to detect autoantibodies is immobilized to the hydrophilic groups on the Capturer particles.

6. The method according to claim 1, wherein the analyte is an antibody of IgE or IgG type with specificity to allergens.

7. The method according to claim 1, wherein the analyte is an antibody of IgG, IgM or IgA type with specificity to autoantigens.

8. The method according to claim 1, wherein the particles anchoring the Capturer have a size in the range of 0.1-100 µm and the flow channels of the matrix have a smallest inner dimension in the range of 0.4-100 µm.

9. The method according to claim 1, wherein the particles which anchor the Capturer have a size in the range of 0.1-1000 µm.

10. The method according to claim 1, wherein the particles which anchor the Capturer have a size in the range of 0.1-100 µm.

11. The method according to claim 1, wherein the labeled particles in the Reactant* have a diameter in the range of 0.01-5 µm.

12. The method according to claim 1, wherein the flow channels have a smallest inner diameter in the range of 0.4-1000 µm.

13. The method according to claim 1, wherein the flow channels have a smallest inner dimension in the range of 0.4-100 µm.

14. The method according to claim 1, wherein the labeled particles are fluorescent or coloured.

15. The method according to claim 1, wherein the Reactant* is predeposited in the matrix upstream of the DZ.

16. The method according to claim 15, wherein the Reactant* is predeposited in the matrix upstream of a sample application site.

17. The method according to claim 1, wherein the particles which anchor the Capturer to the matrix are a synthetic polymer, a semisynthetic polymer or a biopolymer, which on its surface exhibits hydrophilic groups.

18. The method according to claim 1, wherein the Reactant* is captured in the DZ by formation of a ternary complex of Reactant'-analyte-Reactant*, wherein the Reactant* binds to the analyte simultaneously or in sequence and Reactant' is the firmly anchored Capturer or a reactant to which the Capturer binds by biospecific affinity.

19. The method according to claim 18, wherein the analyte is an antigen and the Reactant' and Reactant* are antibodies with specificity for epitopes on the analyte.

20. The method according to claim 1, wherein the method is performed in connection with diagnosing allergy or autoimmune disease.

21. A test kit for performing analytical methods in a flow matrix, which methods utilize biospecific affinity reactions to detect an analyte in a sample, which kit comprises (i) a flow matrix having a detection zone (DZ), in which there is a firmly anchored biospecific affinity reactant (Capturer), and (ii) and analytically detectable reactant (Reactant*),
wherein
   A) the Reactant* has labeled particles as an analytically detectable group, and
   B) the Capturer is anchored to the matrix by immobilized particles which exhibit hydrophilic groups on their surface, wherein the hydrophilic groups are hydroxy, carboxy, amino or sulphonate groups and wherein the particles anchoring the Capturer have a diameter smaller than a smallest inner dimension of the flow channels and do not interfere with detection of Reactant* in the detection zone.

22. The kit according to claim 21, wherein immobilization of a biospecific affinity reactant by covalent binding is to the hydrophilic groups on the Capturer particles.

23. The kit according to claim 21, wherein immobilization of a complex mixture of biospecific affinity reactants is to the hydrophilic groups on the Capturer particles.

24. The kit according to claim 21, wherein immobilization of a complex mixture of biospecific affinity reactants found in allergen extracts is to the hydrophilic groups on the Capturer particles.

25. The kit according to claim 21, wherein immobilization of a complex mixture of biospecific affinity reactants found in biological material used to detect autoantibodies is to the hydrophilic groups on the Capturer particles.

26. The kit according to claim 21, wherein the analyte is an antibody of IgE or IgG type with specificity to allergens.

27. The kit according to claim 21, wherein the analyte is an antibody of IgG, IgM or IgA type with specificity to autoantigens.

28. The kit according to claim 21, wherein the particles anchoring the Capturer have a size in the range of 0.1-100 μm and the flow channels of the matrix have a smallest inner dimension in the range of 0.4-100 μm.

29. The kit according to claim 21, wherein the particles which anchor the Capturer have a size in the range of 0.1-1000 μm.

30. The kit according to claim 21, wherein the particles which anchor the Capturer have a size in the range of 0.1-100 μm.

31. The kit according to claim 21, wherein the labeled particles in the Reactant* have a diameter in the range of 0.01-5 μm.

32. The kit according to claim 21, wherein the flow channels have a smallest inner dimension in the range of 0.4-1000 μm.

33. The kit according to claim 21, wherein the flow channels have a smallest inner dimension in the range of 0.4-100 μm.

34. The kit according to claim 21, wherein the labeled particles are fluorescent or coloured.

35. The kit according to claim 21, wherein the Reactant* is predeposited in the matrix upstream of the DZ.

36. The kit according to claim 35, wherein the Reactant* is predeposited in the matrix upstream of a sample application site.

37. The kit according to claim 21, wherein the particles which anchor the Capturer to the matrix are a synthetic polymer, a semisynthetic polymer or a biopolymer, which on its surface exhibits hydrophilic groups.

38. The kit according to claim 21, wherein the Reactant* is captured in the DZ by formation of a ternary complex of Reactant'-analyte-Reactant*, wherein the Reactant* binds to the analyte simultaneously or in sequence and Reactant' is the firmly anchored Capturer or a reactant to which the Capturer is capable of binding by biospecific affinity.

39. The kit according to claim 38, wherein the analyte is an antigen and the Reactant' and Reactant* are antibodies with a specificity for epitopes on the analyte.

40. The kit according to claim 21, wherein the method is performed in connection with diagnosing allergy or autoimmune disease.

* * * * *

UNITED STATES PATENT AND TRADEMARK OFFICE
CERTIFICATE OF CORRECTION

PATENT NO. : 7,405,084 B1
APPLICATION NO. : 09/582808
DATED : July 29, 2008
INVENTOR(S) : Ib Mendel-Hartvig et al.

It is certified that error appears in the above-identified patent and that said Letters Patent is hereby corrected as shown below:

Claim 21, column 15, line 13, after "(ii)", delete "and".

Signed and Sealed this

Thirtieth Day of September, 2008

JON W. DUDAS
*Director of the United States Patent and Trademark Office*